(12) United States Patent
Kawakita et al.

(10) Patent No.: US 6,702,788 B2
(45) Date of Patent: Mar. 9, 2004

(54) CATHETER

(75) Inventors: Taisei Kawakita, Fujinomiya (JP); Takashi Kaneko, Fujinomiya (JP); Tomoyuki Iida, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/282,213

(22) Filed: Mar. 31, 1999

(65) Prior Publication Data

US 2003/0045842 A1 Mar. 6, 2003

(30) Foreign Application Priority Data

Mar. 31, 1998 (JP) .......................... 10-086255

(51) Int. Cl.7 ........................ A61M 25/00; A61M 5/00
(52) U.S. Cl. ..................................... 604/264
(58) Field of Search ..................... 604/48, 508, 264, 604/523, 532

(56) References Cited

U.S. PATENT DOCUMENTS

| 4,573,476 | A | | 3/1986 | Ruiz | |
|---|---|---|---|---|---|
| 4,694,838 | A | * | 9/1987 | Wijayarthna et al. | 604/532 |
| 4,755,176 | A | * | 7/1988 | Patel | 604/264 |
| 4,795,439 | A | * | 1/1989 | Guest | 604/264 |
| 5,037,403 | A | * | 8/1991 | Garcia | 604/532 |
| 5,180,364 | A | | 1/1993 | Ginsburg | |
| 5,180,387 | A | * | 1/1993 | Ghajar et al. | 604/266 |
| 5,201,723 | A | * | 4/1993 | Quinn | 604/264 |
| 5,599,304 | A | * | 2/1997 | Shaari | 604/94.01 |
| 5,643,228 | A | | 7/1997 | Schucart et al. | |
| 5,800,407 | A | * | 9/1998 | Eldor | 604/264 |

FOREIGN PATENT DOCUMENTS

| JP | 3-37631 | 8/1991 |
|---|---|---|
| JP | 5-28347 | 4/1993 |

* cited by examiner

*Primary Examiner*—Brian L. Casler
*Assistant Examiner*—Michael M Thompson
(74) *Attorney, Agent, or Firm*—Burns, Doane, Swecker & Mathis, LLP

(57) ABSTRACT

A catheter of the present invention is used for angiography and has a tube body (catheter tube) having a lumen, a front end opening communicating with the lumen, and a side aperture communicating with the lumen. The side aperture is obliquely formed from the inner peripheral surface of the tube body to the peripheral surface thereof, namely, from the inner side of the tube body to the outer side thereof such that the side aperture is directed toward the front side of the tube body.

25 Claims, 7 Drawing Sheets

CATHETER

BACKGROUND OF THE INVENTION

The present invention relates to a catheter such as an angiographic catheter for use in an image formation of the heart or of tissues on the periphery thereof and a catheter for injecting a liquid medicine into a desired part of a human body.

As well known, including coronary angiography for checking the state of the blood vessel of the heart, a selective angiography for checking the states of blood vessels has been performed by injecting a contrast medium into branch portions of the blood vessels through a catheter, with the front end thereof inserted thereinto. For example, as catheters for use in the coronary angiography, a Judkins type catheter and an Amplatz type catheter are known. Normally, these catheters are introduced into the blood vessel from the femoral artery by a Seldinger method or a sheath method to perform selective coronary angiography.

In this case, some catheters are used for the angiography of the right coronary artery only, while other catheters are used for the angiography of the left coronary artery only. In recent years, a catheter which can be used for the angiography of both the right and left coronary arteries has been developed and is in use.

In the case the catheter for use in the angiography, a type having a side aperture formed at the front end thereof and a type not having a side aperture formed at the front end thereof are used.

In the catheter having the side aperture formed at the front end thereof, blood flows into the catheter from the side aperture. Thus, the pressure inside the catheter is maintained at an approximately constant pressure. Therefore, the catheter of this type has an advantage that when the front end of the catheter is inserted deep into the coronary artery, it is possible to prevent the inside of the catheter from becoming almost vacuum. Thus, it does not occur that it is difficult to pull the catheter from the coronary artery, i.e., it does not occur that the catheter is wedged in the coronary artery. Further, when a contrast medium is jetted to a desired blood vessel part under a high pressure from the front end of the catheter, a part of the contrast medium leaks out from the side aperture. Thus, the contrast medium is jetted out from the front end of the catheter at a reduced speed. Therefore, it is possible to prevent the front end of the catheter from being dislocated from a blood vessel branch portion at the time of the coronary angiography (at the time of injection of contrast medium).

However, the side aperture of the conventional catheter is open at a right angle with the axial direction of the catheter. Thus, it often occurs that the contrast medium discharged from the side aperture does not flow into a desired blood vessel part but often leaks downstream from the blood vessel branch portion. Consequently, a small absolute amount of the contrast medium flows to the desired blood vessel part. That is, the conventional catheter has a low degree of angiographic performance.

In the catheter not having the side aperture formed at the front end thereof, the contrast medium is all jetted toward a desired blood vessel part. But the contrast medium is jetted from the front end of the catheter at a high speed. Thus, a portion having a pressure higher than a pressure-jetted portion is generated forward from the pressure-jetted portion, and hence the contrast medium flows backward therefrom to the blood vessel branch portion. Consequently, the contrast medium does not flow into the desired blood vessel part but leaks downstream from the blood vessel branch portion. In order to enhance the angiographic performance of the catheter, it is necessary to flow the contrast medium more to the desired blood vessel part at a higher pressure because of the contrast medium has leaked. In this case, it is very likely that the front end of the catheter is dislocated from the blood vessel branch portion during the angiographic operation.

The smaller the diameter of the catheter is, the smaller is the diameter of the stream of the contrast medium discharged from the front end of the catheter. Thus, it is difficult to form the image of the inlet of the coronary artery (blood vessel branch portion). In order to form the image of the inlet of the coronary artery reliably, the injection pressure (discharge pressure) of the contrast medium is raised to increase the backward flow amount of the contrast medium.

As described above, when the catheter having the side aperture formed at the front end thereof is used, it often occurs that the contrast medium discharged from the side aperture does not flow into the desired blood vessel part. When the catheter not having the side aperture formed at the front end thereof is used, the contrast medium discharged from the front end thereof flows backward because the contrast medium is jetted from the front end thereof at a high speed. That is, the catheter of each of both types does not provide reliable angiographic performance. Thus, there is a growing demand for the development of a catheter capable of solving the problems of the catheter of both types and having reliable angiographic performance.

It is an object of the present invention to provide a catheter capable of jetting a liquid from the front end thereof at a low speed, preventing the front end thereof from being dislocated from a blood vessel branch portion, preventing the liquid from flowing backward, and reducing the amount of the liquid which leaks from a desired part.

It is another object of the present invention to provide a catheter capable of jetting a contrast medium from the front end thereof at a low speed, preventing the front end thereof from being dislocated from a blood vessel branch portion, preventing the contrast medium from flowing backward, reducing the amount of the contrast medium which leaks from a desired part whose image is to be formed, and being reliable in an image formation performance. The catheter which achieves the above object is, for example, an angiographic catheter for use in coronary angiography or the like for performing a selective image formation by inserting a front end thereof into a branch portion of a blood vessel.

It is still another object of the present invention to provide a catheter capable of forming the image of an inlet of the coronary artery securely, without injecting a contrast medium to a desired part at a high pressure.

SUMMARY OF THE INVENTION

The catheter of the present invention has a tube body having a lumen, a front end opening communicating with the lumen, and a side aperture communicating with the lumen. The side aperture is obliquely formed from an inner peripheral surface of the tube body toward an outer peripheral surface thereof such that the side aperture is directed toward a front side of the tube body.

DETAILED DESCRIPTION OF THE PREFERRED EMBODIMENTS

Figure 1:
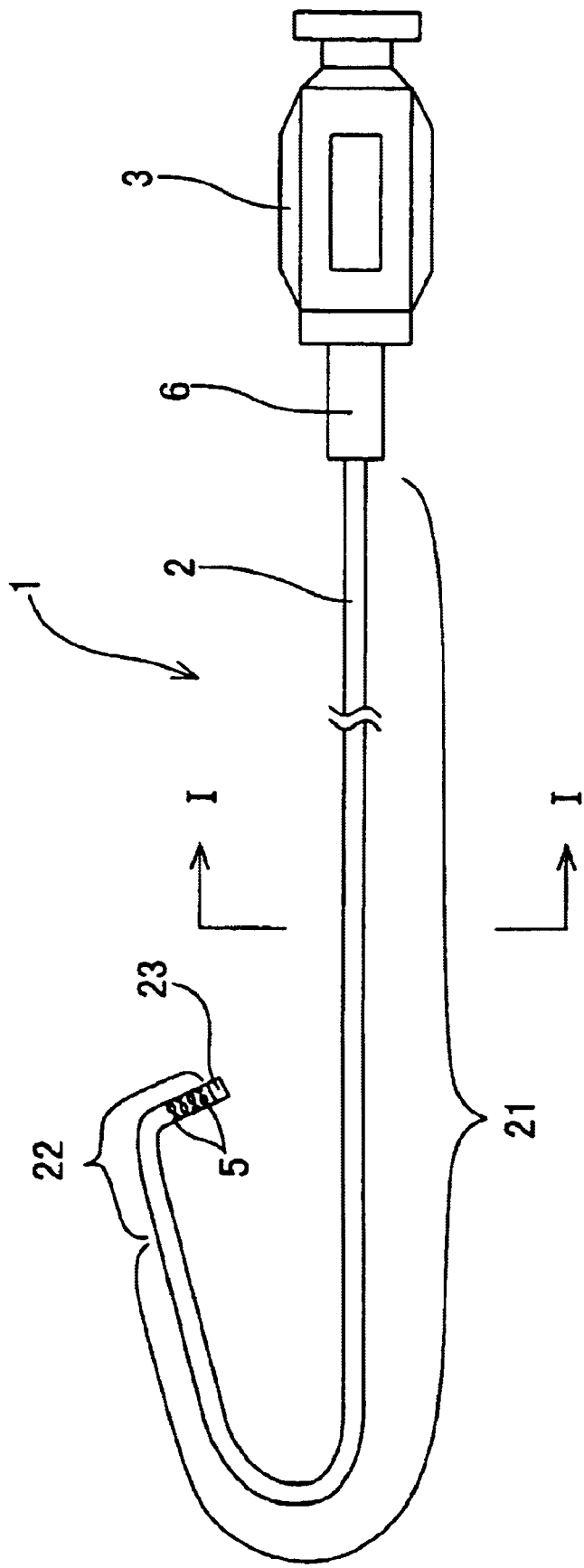
FIG. 1 is a plan view showing a catheter according to an embodiment of the present invention.

The catheter of the present invention will be described with reference to embodiments.

A catheter 1 of the present invention is used for angiography and has a tube body (catheter tube) 2 having a lumen 4, a front end opening 7 communicating with the lumen 4, and a side aperture 5 communicating with the lumen 4. The side aperture 5 is obliquely formed from an inner peripheral surface of the tube body 2 to an outer peripheral surface thereof such that the side aperture 5 is directed toward the front side of the tube body 2.

More specifically, the catheter 1 of the present invention includes the tube body 2; the liquid-introducing lumen 4 formed inside the tube body 2 and open at the front end of the tube body 2; a base part 3 connected with a rear end of the tube body 2 and allowing a liquid to be introduced into the liquid-introducing lumen 4 so that the liquid is injected into a human body; and the side aperture 5 formed at a front part (portion) of the tube body 2 and communicating with the liquid-introducing lumen 4. The side aperture 5 is formed obliquely with respect to the axis (center line) of the tube body 2 from the inner peripheral surface of the tube body 2 to the outer peripheral surface thereof such that the side aperture 5 is directed toward the front side of the tube body 2. More specifically, the side aperture 5 is formed such that an extension line of the center line thereof intersects with the center line of the tube body 2 at an acute angle at the front side of the intersection.

The catheter 1 having the construction is of Judkins type and used for the angiography of the left coronary artery. An example of the construction of the catheter 1 will be described in detail below. The present invention is applicable not only to the Judkins type, but also to Amplatz type, a type for use in the angiography of the right coronary artery, and a type for use in the angiography of the right and left coronary arteries.

The present invention is not limited to the catheter for the coronary angiography, but applicable to various types of angiographic catheters for the belly, the head, and like for performing a selective angiography by inserting the front end thereof into a branch portion of a blood vessel and also applicable to liquid medicine injection catheters for injecting various liquid medicines into various desired parts to treat affected parts of a human body.

The catheter 1 of the embodiment shown in FIG. 1 has the flexible tube body 2 and the base part (hub) 3 connected with the rear end of the tube body 2.

The outer diameter of the tube body 2 is favorably 2.7 mm or less throughout the catheter 1 and more favorably 2.0 mm or less. The entire length of the tube body 2 is favorably 50–125 cm and more favorably, 80–100 cm.

Figure 2:
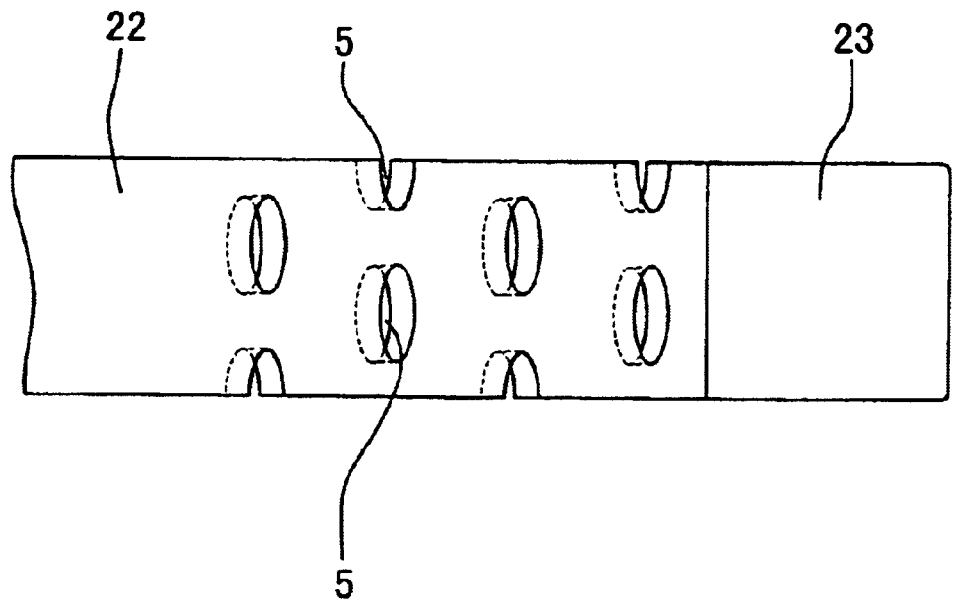
FIG. 2 is an enlarged plan view showing a front end part of the catheter according to the embodiment of the present invention.
Figure 3:
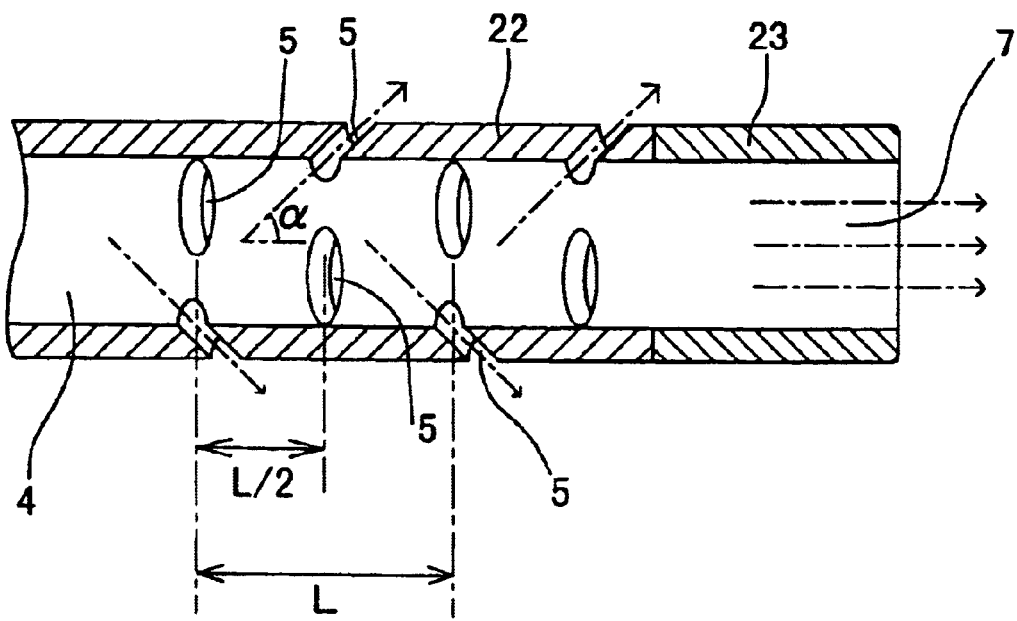
FIG. 3 is an enlarged sectional view showing the front end part of the catheter according to the embodiment of the present invention.

The tube body 2 has a highly rigid main part 21, a front flexible part 22, and a soft tip part 23. As shown in FIGS. 2 and 3, inside the tube body 2, the liquid-introducing lumen 4 opening at the front end of the tube body 2 is formed from the rear end of the tube body 2 to the front end thereof.

In inserting the catheter 1 into a desired part (objective part) of a human body, a guide wire is inserted into the lumen 4. In injecting a contrast medium into the desired part, the contrast medium is injected thereinto from the front end opening 7 of the lumen 4 through the lumen 4.

The inner diameter of the lumen 4 is set to 0.9–1.8 mm and set to favorably, 1.0–1.5 mm.

The rear end of the tube body 2 is covered with a kink prevention tube 6 for preventing the rear end of the tube body 2 from bending (kinking). As the material to form the kink prevention tube 6, a resinous material such as crosslinked polyolefin, silicone, and the like or metal such as stainless steel can be preferably used.

The base part 3 is used to introduce a liquid contrast medium and the guide wire to lumen 4 so that the liquid contrast medium and the guide wire are injected into a desired part of a human body. For example, a syringe (not shown) containing the contrast medium or the like is connected with the rear end of the base part 3 to jet the contrast medium or the like to the desired part from the front end of the catheter 1 through the base part 3 and the lumen 4. Gripping the base part 3, an operator performs an insertion operation to insert the catheter 1 into the human body and a removal operation to remove the catheter 1 therefrom.

As the material to form the base part 3, the following hard thermoplastic resin can be preferably used: polycarbonate; polypropylene; polyamide; polysulfone; polyarylate; and methacrylate-butylene-styrene copolymer.

As shown in FIGS. 2 and 3, a plurality of side apertures 5 is formed on the front part of the tube body 2. In the embodiment, a plurality of side apertures 5 is formed on the front flexible part 22 of the tube body 2. In the embodiment, the side aperture 5 is formed in the shape of an ellipse long in the circumferential direction (direction perpendicular to the axial direction of the tube body 2) of the tube body 2. The angle (α) of the side aperture 5 which is long in the circumferential direction of the tube body 2 with respect to the axis (center axis) of the tube body 2 (lumen 4) can be made to be smaller than the angle (α) of a side aperture (described later with reference to FIGS. 8 through 10) which is long in the axial direction of the tube body 2 with respect to the axis thereof. Thus, the contrast medium can be jetted to the desired part from the side aperture 5 reliably.

Two side apertures 5 are arranged in six rows such that in every row, the centers of the two side aperture 5 are spaced at a predetermined distance L in the lengthwise direction of the tube body 2. (In other words, the side apertures 5 are arranged at an equal angle). Thus, in total, 12 side apertures are formed on the front flexible part 22 of the tube body 2.

Referring to FIGS. 2 and 3, the side apertures 5 are arranged in the lengthwise (axial) direction of the tube body 2 by axially dislocating the side apertures 5 of a row by half (L/2) of the distance L with respect to the positions of the side apertures 5 of an adjacent row. Thus, the side apertures 5 are arranged substantially uniformly in the circumferential and lengthwise directions of the tube body 2. Because a plurality of side apertures 5 is not formed concentratively in a predetermined region, it is possible to prevent the strength of a part of the tube body 2, namely, the side aperture-forming region from being lower than other regions thereof. Thus, it is possible to prevent the side aperture-forming region of the catheter 1 (front flexible part 22) from being bent or broken. Further, the jet speed of the contrast medium can be preferably reduced by forming the side apertures 5 on the tube body 2 scatteringly.

In the present invention, the number of the side apertures 5 and the location thereof are not limited to those shown in the drawing. For example, it is possible to form only one side aperture 5 or a plurality thereof in a row on the tube body 2. It is also possible to form one side aperture 5 or more than two side apertures 5 in each row on the tube body 2. It is also possible to form a large number of side apertures 5 irregularly on the tube body 2.

The shape of the side aperture 5 is not limited to the elliptical shape shown in FIGS. 2 and 3, but may be formed in any desired shapes. For example, the side aperture 5 may be formed in the shape of an ellipse long in the lengthwise direction of the tube body 2, circular or polygonal (pentagonal, hexagonal, and the like).

As shown in FIGS. 2 and 3, the side aperture 5 communicates with the lumen 4 and is formed obliquely with respect to the axis (center line) of the tube body 2 from the inner peripheral surface of the tube body 2 to the peripheral surface thereof such that the side aperture 5 is directed toward the front side of the tube body 2. In other words, the side aperture 5 is obliquely formed from the inner peripheral surface of the tube body 2 to the peripheral surface thereof such that the side aperture 5 is directed toward the front side of the tube body 2.

Accordingly, as shown with arrows of FIG. 3, the contrast medium introduced into the lumen 4 from the base part 3 is jetted from the front end of the catheter 1, with a part of the contrast medium leaking out from the side aperture 5. Thus, the contrast medium is jetted at a low speed, which prevents the contrast medium introduced into a desired part from being flowed backward and allows the contrast medium discharged from the side aperture 5 to be jetted toward the front end of the catheter 1. Therefore, it is possible to flow the contrast medium discharged from the side aperture 5 into a desired blood vessel branch portion. Accordingly, it is unnecessary to flow a large amount of the contrast medium to the desired part by applying a high pressure thereto at the base part 3. This is because it is possible to inject a sufficient amount of contrast medium from the side aperture 5 as well as the front end opening 7 of the catheter 1. Thus, stable angiographic performance can be obtained.

Further, in the catheter of the present invention, because the contrast medium is discharged from the side aperture 5 as well as the front end opening 7, the contrast medium discharged therefrom flows to the desired part as a thick stream (jet) as a whole. Thus, the catheter is superior in forming the image of the inlet (blood vessel branch portion) of the coronary artery. Unlike the conventional catheter, it is unnecessary to apply a high discharge pressure to the contrast medium to reliably form the image of the inlet of the coronary artery by flowing the contrast medium backward.

The size of the side aperture 5 is not limited to any specific value because it is determined in consideration of the number of the side apertures 5, the outer diameter of the tube body 2, and the kind of the material of the tube body 2. When the side aperture 5 is formed in the shape of an ellipse long in the circumferential direction of the tube body 2 as shown in FIGS. 2 and 3, the length of the major axis of the ellipse is preferably in the range of 0.4–0.6 mm, and the length of the minor axis thereof is preferably in the range of 0.2–0.4 mm. The size (diameter, major axis or the like) of the side aperture 5 is preferably 0.10–0.43 times as large as the outer diameter of the tube body 2. The sectional area (circle, ellipse or the like) of the side aperture 5 is preferably in the range of 0.06–0.19 mm$^2$. The front end of the side aperture-forming region is spaced preferably at 1.5–2.5 mm from the front end of the tube body 2. The length of the side aperture-forming region is preferably in the range of 3.5–5.0 mm in the lengthwise direction of the tube body 2.

In the case where a plurality of the side apertures 5 is formed in a row, the distance (L) between the adjacent side apertures 5 in the axial direction of the tube body 2 is preferably in the range of 0.5–1.5 mm.

The side aperture 5 inclines at an angle ($\alpha$) 20°–60° and favorably at 30°–45° with respect to the axis of the tube body 2 (lumen 4). If the inclination ($\alpha$) dose not exceeds 60°, it is easy to flow the contrast medium jetted out from the side aperture 5 into the desired part, and much contrast medium leaks downstream from the blood vessel branch portion. That is, it is easy to obtain a favorable angiographic performance. If the inclination ($\alpha$) is more than 20°, the formation direction of the side aperture 5 is not too proximate to the lengthwise (axial) direction of the tube body 2. Consequently, it is easy to form the side aperture 5. Further, if the inclination ($\alpha$) is more than 20°, the axial length of the side aperture 5 is not too large, i.e., the distance between the surface thereof flush with the inner peripheral surface of the tube body 2 and the surface thereof flush with the peripheral surface of the tube body 2 is large. In this case, a large force is required to jet the contrast medium from the side aperture 5. That is, it is easy to discharge the contrast medium from the side aperture 5. The inclinations of the side apertures 5 are not necessarily equal to each other. For example, the inclination of the side aperture 5 of an odd row may be smaller (or larger) than that of the side aperture 5 of an even row. Further, the side apertures of a row may have different inclinations.

Figure 5:
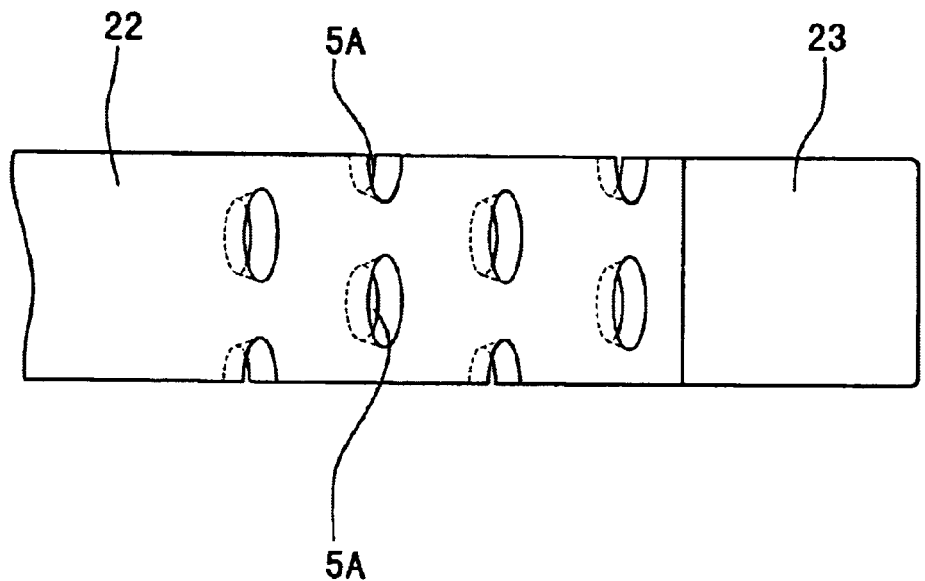
FIG. 5 is an enlarged plan view showing a front end part of a catheter according to another embodiment of the present invention.
Figure 6:
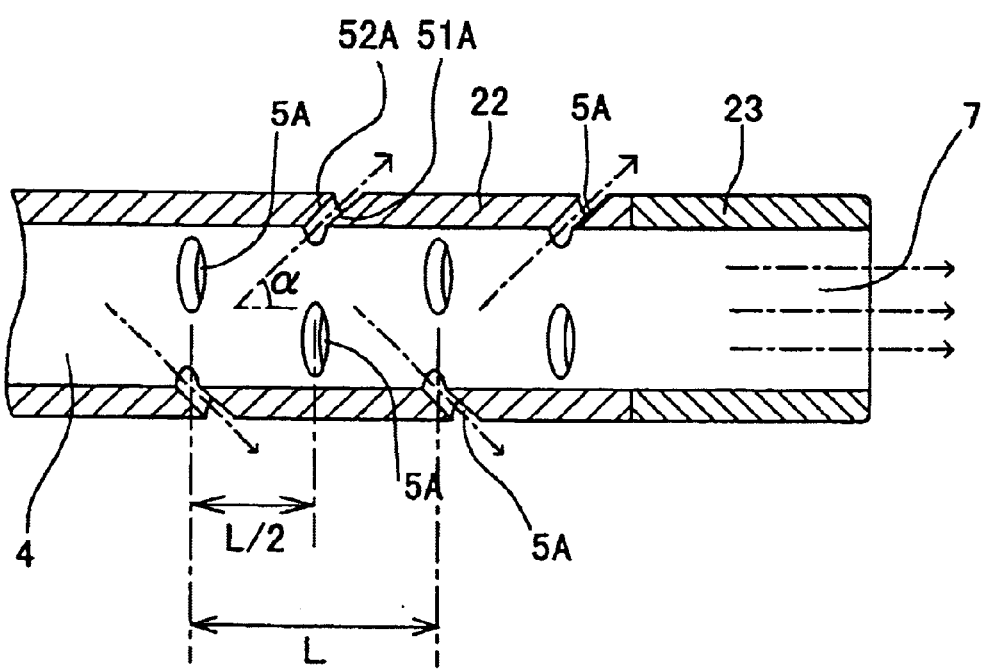
FIG. 6 is an enlarged sectional view showing the front end part of the catheter according to the embodiment of the present invention.
Figure 7:
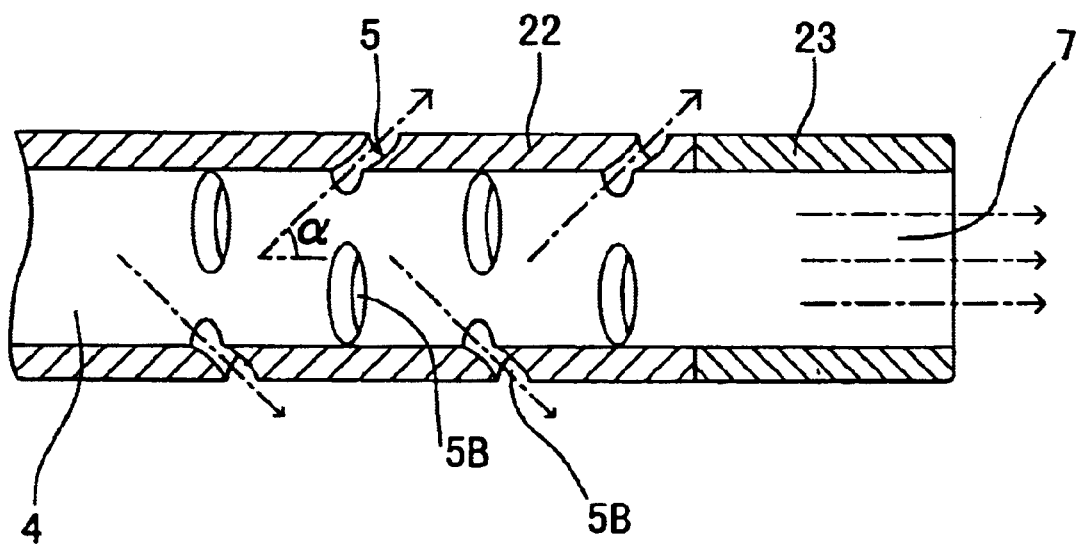
FIG. 7 is an enlarged sectional view showing a front end part of a catheter according to still another embodiment of the present invention.

The form of the side aperture 5 of the present invention is not limited to that shown in FIGS. 2 and 3. For example, as shown in FIGS. 5 and 6, a side aperture 5A may be so formed that the inclination of an end surface 51A thereof at the front side in the axial direction of the tube body 2 with respect to the axial direction of the tube body 2 is different from that of an end surface 52A thereof at the rear side in the axial direction thereof with respect to the axial direction of the tube body 2. Further, as shown in FIG. 7, a part of the end surface of a side aperture 5B or the entirety thereof is not necessarily formed as a flat inclined plane but may be a gently curved inclined plane. In the case of the catheter shown in FIGS. 5, 6, and 7, an angle ($\alpha$) in the range of 20–60° and favorably, an angle ($\alpha$) in the range of 30–45° is formed between the axis of the tube body 2 and the axis of each of the side apertures 5A and 5B connecting with each other the center of a virtual surface thereof flush with the inner peripheral surface side of the tube body 2 and the center of a virtual surface thereof flush with the outer peripheral surface of the tube body 2.

The method of forming the side aperture 5 is not limited to a specific one. The side aperture 5 can be formed by machining. It is favorable to form the side aperture 5 by laser beam machining because the side aperture 5 can be formed easily and the shape and dimension thereof can be controlled with high precision. Of the laser beam machining, it is more favorable to use a laser that oscillates at a wavelength within an ultraviolet region. In particular, an excimer laser can be preferably used.

The excimer laser achieves short pulse oscillation with a high peak power in the ultraviolet region. By combining noble gas (Ar, Kr, Xe, and the like) with halogen (F, Cl, Br, and the like), the excimer laser oscillates, for example, at a wavelength ranging from 193 to 351 nm. The excimer laser having such a property allows the side aperture 5 of a small diameter to be formed easily with high processability as well as high precision, without causing process errors such as alteration, meltdown, flash, and soot.

Taking into account the materials constituting the catheter 1, the excimer laser that oscillates at a wavelength of less than 248 nm is preferred. More specifically, a KrF excimer laser that oscillates at a wavelength of less than 248 nm or an ArF excimer laser that oscillates at a wavelength of less than 193 nm is preferred. Lasers with such a wavelength provide a remarkable high processability.

It is possible to use a solid laser as a light source, utilizing wavelength conversion technology. The solid laser oscillates at a wavelength within the ultraviolet region.

Figure 4:
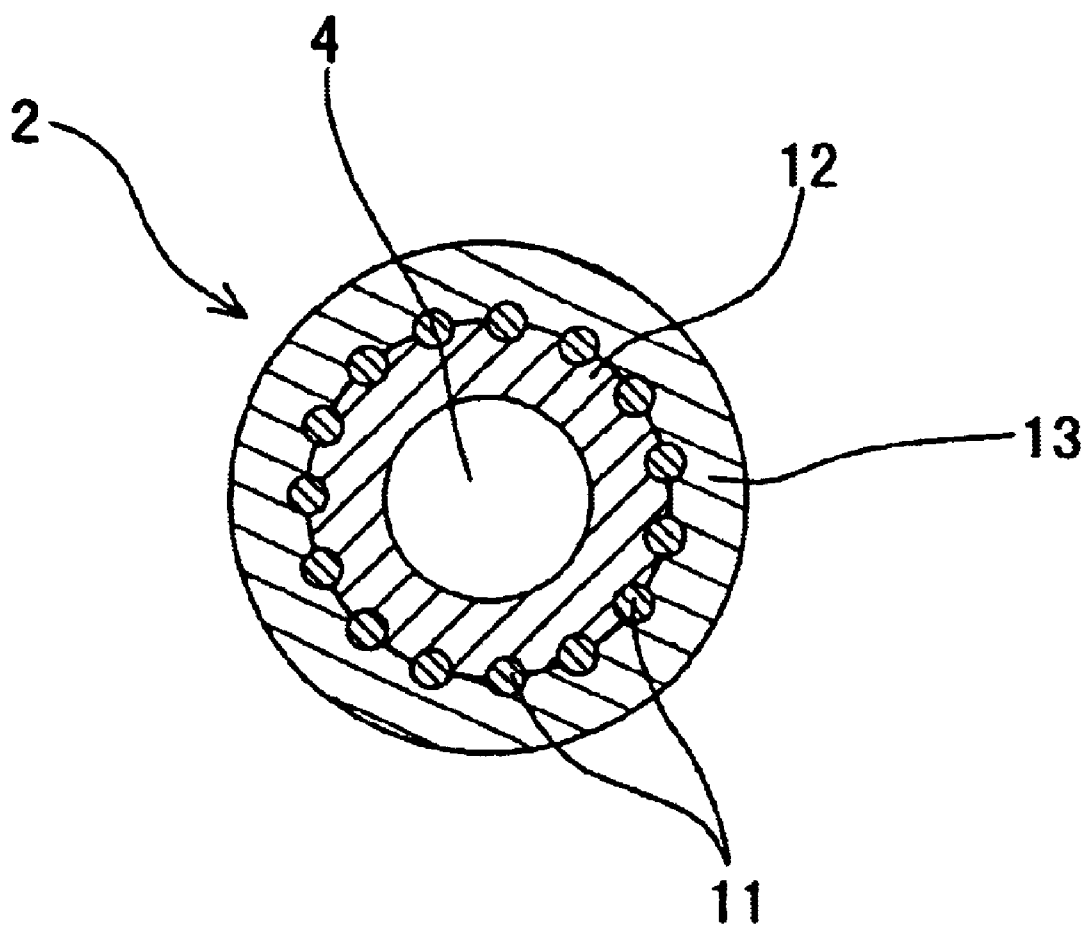
FIG. 4 is a sectional view taken along a line I—I of FIG. 1.

As shown in FIG. 4, the main part 21 of the tube body 2 has a metal mesh 11 serving as a reinforcing material extending in the lengthwise direction of the tube body 2. The metal mesh 11 is embedded in the tube body 2 in almost the entirety thereof except the front flexible part 22.

The reinforcing material prevents the main part 21 of the catheter 1 from being bent and enhances the torque transmission performance of the catheter 1. The reason the reinforcing material is not provided rearward in a predetermined length from the front end of the tube body 2 is as follows: If the reinforcing material is provided in the front end of the tube body 2, the front end of the catheter 1 may injure blood vessel walls and further, the catheter 1 may be hard at the front end thereof. Consequently, it is difficult to insert the front end of the catheter 1 into the coronary artery.

The tube body 2 of the catheter 1 of the embodiment is constituted of an inner layer 12 forming the lumen 4 penetrating the tube body 2 from the rear end thereof to the front end thereof; and an outer layer 13 covering the inner layer 12. The metal mesh 11 is embedded in the boundary between the inner layer 12 and the outer layer 13. The inner layer 12 and the outer layer 13 extend toward the front side beyond the front end of the metal mesh 11, thus constituting the front flexible part 22.

The material to form the inner layer 12 and the outer layer 13 is selected from polyamide resin (for example, nylon 11, nylon 12, and nylon 6); polyester polyamide resin (for example, Grilax (trade name), product of DIC Corp.); polyether polyamide resin (for example, Pebax (trade name), product of Atochem Corp.); and polyurethane resin. These resinous materials can be used singly, and in addition, may be used as a mixture obtained by blending two or more thereof with each other or used as a polymer alloy by copolymerizing two or more thereof. The polymer alloy (copolymerization) is a concept including polymer blend, graft copolymer, block copolymer, and random copolymer.

The catheter 1 is inserted into a desired part of a human body while the position of the front end of the catheter 1 is being checked with X-rays being applied to the human body. Therefore, it is preferable for the material of the tube body 2 to contain a radiographical substance such as barium sulfate, bismuth oxide, and tungsten.

The inner layer 12 and the outer layer 13 are bonded to each other with an adhesive agent, fused to each other or formed integrally with each other by coating molding.

The metal mesh 11 is constituted of a metal wire consisting of a super-elastic alloy such as stainless, an alloy of nickel and titanium, an amorphous alloy or the like. The metal mesh 11 has a diameter of about 0.01–0.2 mm. The length of the metal mesh-unprovided region is set appropriately according to the quality of a material of the tube body 2, the inner diameter thereof, and the outer diameter (sum of inner layer, intermediate layer, and outer layer) thereof.

The soft tip part 23 is formed at the front side of the front flexible part 22 of the tube body 2. The soft tip part 23 is formed more softly than the front flexible part 22. When coronary angiography is performed by using the catheter 1, the soft tip part 23 is inserted into the inlet of the coronary artery.

Materials more softer, namely, more flexible than the material of the main part 21 and that of the front flexible part 22 (material of the inner and outer layers 12 and 13) are selectively used as the material of the soft tip part 23. In order to connect the soft tip part 23 and the front flexible part 22 with each other easily and at a high degree of strength, it is preferable that the material to form the front flexible part 22 and the material to form the soft tip part 23 are compatible with each other. Compatibility means that thermodynamic mutual solubility of both materials is favorable. In other words, the material of the front flexible part 22 and that of the soft tip part 23 do not separate from each other after they are hardened.

As preferable combinations of materials compatible with each other, nylon 12 or a block copolymer of polyether and polyamide is selected as the material of the main part 21 and the front flexible part 22, and a polyamide elastomer more flexible than the block copolymer of polyether and polyamide is selected as the material of the soft tip part 23. In this case, the main part 21 and the front flexible part 22 are both made of polyamide resin. As another preferable combination, polyurethane is selected as the material of the soft tip part 23, and a polymer alloy of the polyamide elastomer and the polyurethane is selected as the material of the main part 21 and the front flexible part 22. In this case, the main part 21 and the front flexible part 22 are both made of polyurethane resin.

As in the case of the main part 21 and the front flexible part 22, it is preferable for the soft tip part 23 to contain a radiographical substance. As the radiographical substance, substances similar to the above-described ones can be used.

In the catheter 1 of the embodiment having the soft tip part 23 formed thereon, it is preferable to position the side aperture 5 at the rear side (the front flexible part 22 side) of the soft tip part 23. If the side aperture 5 is formed in both the soft tip part 23 and the front flexible part 22, the soft tip part 23 and the front flexible part 22 are connected with each other at a lower degree of strength and thus the side aperture-forming region may be broken or bent (kinked).

A catheter according to another embodiment of the present invention will be described below with reference to FIGS. 8 through 10.

The fundamental construction of a catheter 30 of the embodiment is the same as that of the catheter 1 of the above-described embodiment except that the configuration of a side aperture 35 of the catheter 30 is different from that of the side aperture 5 of the catheter 1. Thus, like parts are designated by like reference numerals in the embodiment. Thus, refer to the description of the catheter 1 for the description of the same parts of the catheter 30 as those of the catheter 1.

Figure 8:
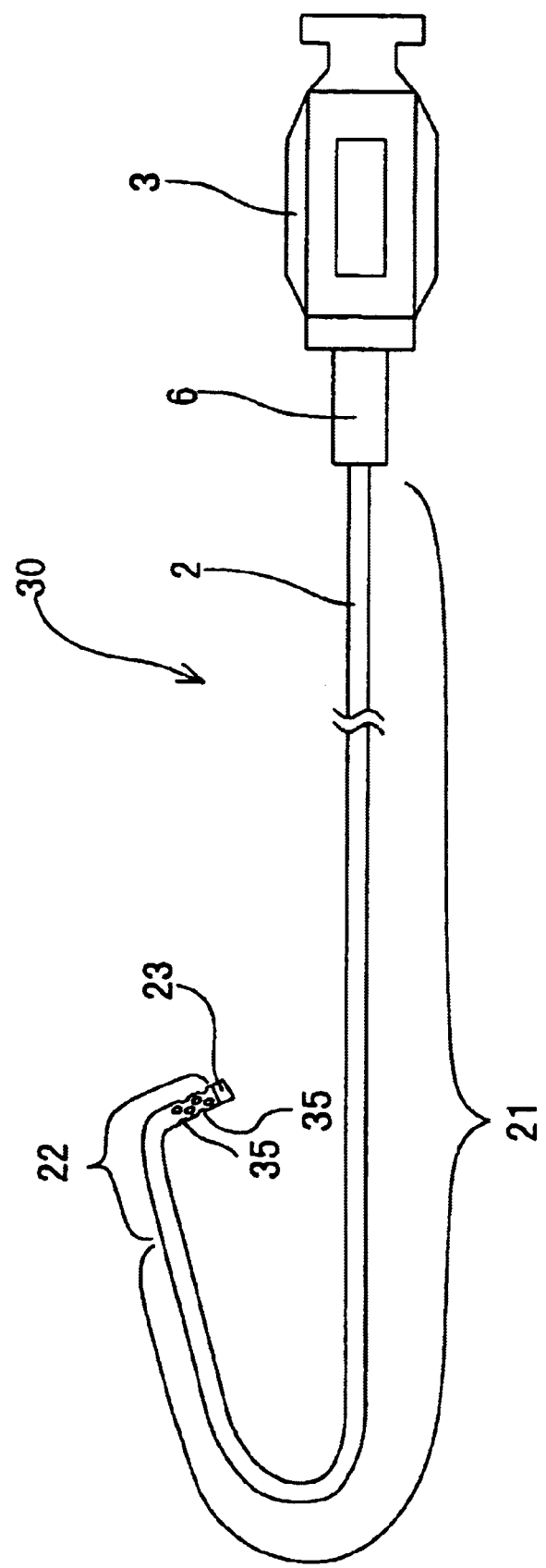
FIG. 8 is a plan view showing a catheter according to still another embodiment of the present invention.

As shown in FIG. 8, similarly to the catheter 1, the catheter 30 of the embodiment has the flexible tube body 2 having a plurality of side apertures 35 formed at a front part thereof and the base part (hub) 3 connected with the rear end of the tube body 2.

The tube body 2 has the highly rigid main part 21, the front flexible part 22, and the soft tip part 23. As shown in FIGS. 9 and 10, inside the tube body 2, the liquid-introducing lumen 4 open at the front end of the tube body 2 is formed from the rear end of the tube body 2 to the front end thereof.

The rear end of the tube body 2 is covered with the kink prevention tube 6 for preventing the rear end of the tube body 2 from bending (kinking). As the material to form the kink prevention tube 6, a resinous material such as crosslinked polyolefin, silicone, and the like or metal such as stainless steel can be preferably used.

Figure 9:
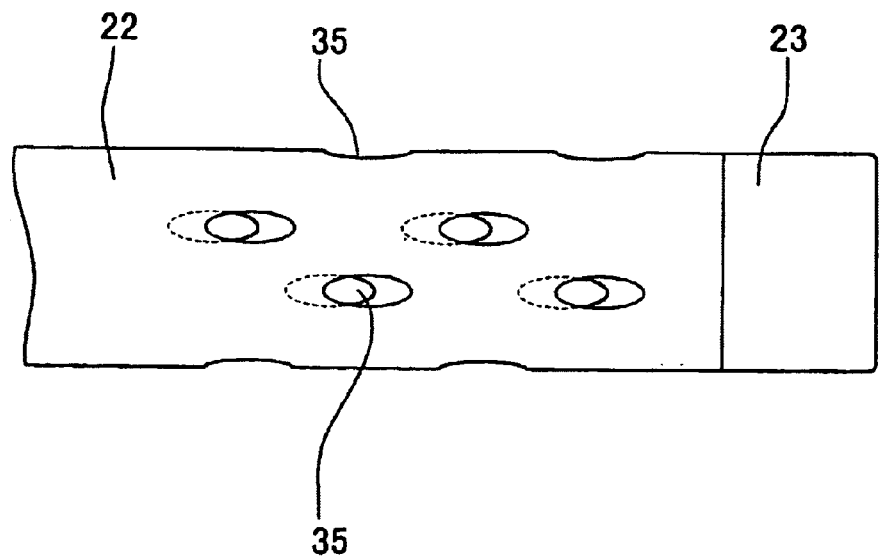
FIG. 9 is an enlarged plan view showing the front end part of the catheter shown in FIG. 8.
Figure 10:
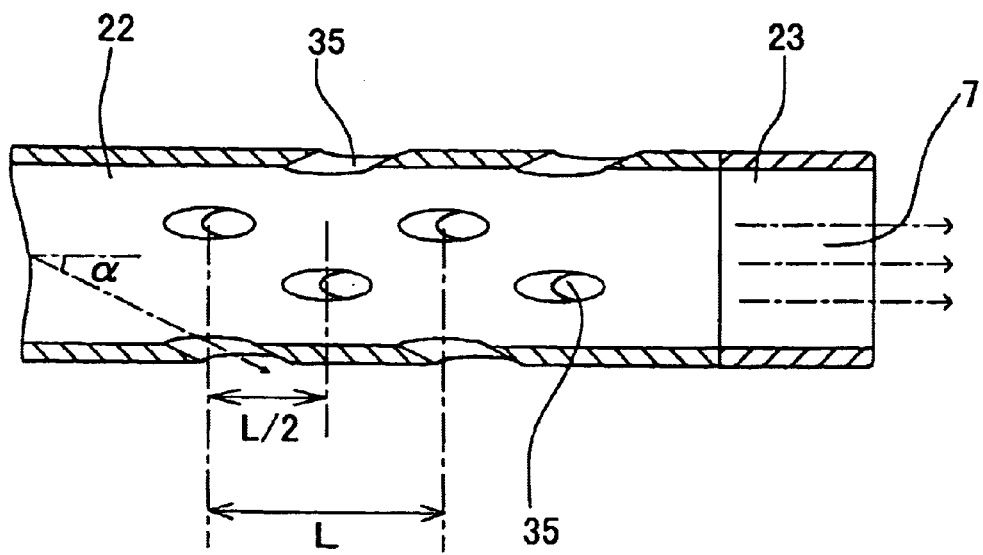
FIG. 10 is an enlarged sectional view showing the front end part of the catheter shown in FIG. 8.

As shown in FIGS. 9 and 10, a plurality of side apertures 35 is formed on the front flexible part 22 of the tube body 2. In the catheter 30, the side aperture 35 is formed in the shape of an ellipse long in the axial direction of the tube body 2 to allow the degree of reduction in the tensile strength of the side aperture-forming region to be small.

Two side apertures 35 are arranged in six rows such that in every row, the centers of the two side aperture 35 are spaced at a predetermined distance L in the lengthwise direction of the tube body 2. (In other words, the side apertures 35 are arranged at an equal angle). Thus, in total, 12 side apertures are formed on the front flexible part 22 of the tube body 2. Referring to FIGS. 9 and 10, the side apertures 35 are arranged in the lengthwise (axial) direction of the tube body 2 by axially dislocating the side apertures 35 of a row by half (L/2) of the distance L with respect to the positions of the side apertures 35 of an adjacent row. Thus, the side apertures 35 are arranged substantially uniformly in the circumferential and lengthwise directions of the tube body 2. Because a plurality of side apertures 35 is not formed concentratively in a predetermined region, it is possible to prevent the strength of a part of the tube body 2, namely, the side aperture-forming region from being lower than other regions thereof. Thus, it is possible to prevent the side aperture-forming region of the catheter 1 (front flexible part 22) from being bent or broken. Further, the jet speed of the contrast medium can be preferably reduced by forming the side apertures 35 on the tube body 2 scatteringly.

In the present invention, the number of the side apertures 35 and the location thereof are not limited to those shown in the drawing. For example, it is possible to form only one side aperture 35 or a plurality thereof in a row on the tube body 2. It is also possible to form one side aperture 35 or more than two side apertures 35 in each row on the tube body 2. It is also possible to form a large number of side apertures 35 irregularly on the tube body 2.

The shape of the side aperture 35 is not limited to the elliptical shape shown in FIGS. 9 and 10, but may be formed in any desired shapes. For example, it may be formed polygonally (pentagonal, hexagonal, and the like) or the like.

As shown in FIGS. 9 and 10, the side aperture 35 communicates with the lumen 4 and is formed obliquely with respect to the axis (center line) of the tube body 2 from the inner peripheral surface of the tube body 2 to the peripheral surface thereof such that the side aperture 35 is directed toward the front side of the tube body 2. In other words, the side aperture 35 is obliquely formed from the inner peripheral surface of the tube body 2 to the peripheral surface thereof such that the side aperture 35 is directed toward the front side of the tube body 2.

Accordingly, as shown with arrows of FIG. 10, the contrast medium introduced into the lumen 4 from the base part 3 is jetted from the front end of the catheter 30 and a part of the contrast medium leaks out from the side aperture 35. The contrast medium discharged from the side aperture 35 is jetted to the front side of the catheter 30. Therefore, it is possible to flow the contrast medium discharged from the side aperture 35 into a desired blood vessel branch portion.

The size of the side aperture 35 is not limited to any specific value because it is determined in consideration of the number of the side apertures 35, the outer diameter of the tube body 2, and the kind of the material of the tube body 2. When the side aperture 35 is formed in the shape of an ellipse long in the axial direction of the tube body 2, as shown in FIGS. 9 and 10, the length of the major axis of the ellipse is preferably in the range of 0.4–0.6 mm, and the length of the minor axis thereof is preferably in the range of 0.2–0.4 mm. The size (diameter, major axis or the like) of the side aperture 35 is preferably 0.10–0.43 times as large as the outer diameter of the tube body 2. The sectional area (circle, ellipse or the like) of the side aperture 35 is preferably in the range of 0.06–0.19 mm$^2$. The front end of the side aperture-forming region is spaced preferably at 1.5–2.5 mm from the front end of the tube body 2. The length of the side aperture-forming region is preferably in the range of 3.5–5.0 mm in the lengthwise direction of the tube body 2. In the case where a plurality of side apertures 35 is formed in a row, the distance between the adjacent side apertures 35 in the axial direction of the tube body 2 is preferably in the range of 0.5–1.5 mm.

The side aperture 35 inclines at an angle ($\alpha$) 20°–60° and favorably at 30°–45° with respect to the axis of the tube body 2 (lumen 4). The inclinations of the side apertures 35 are not necessarily equal to each other. For example, the inclination of the side aperture 35 of an odd row may be smaller (or larger) than that of the side aperture 35 of an even row. Further, the side apertures of the same row may have different inclinations.

The mode of the side aperture 35 of the present invention is not limited to that shown in FIGS. 9 and 10. For example, similarly to the catheters shown in FIGS. 5 and 6, the side aperture may be so formed that the inclination of an end surface thereof at the front side in the axial direction of the tube body 2 with respect to the axial direction of the tube body 2 is different from that of an end surface thereof at the rear side in the axial direction thereof with respect to the axial direction of the tube body 2. In other words, the sectional area of the side aperture of the present invention may increase toward the outer sides of the tube body 2. Further, similarly to the catheter shown in FIG. 7, a part of the end surface of the side aperture of the embodiment or the entirety thereof is not necessarily formed as a flat inclined plane but may be a gently curved inclined plane. In the case where the shape of the side aperture is modified, an angle ($\alpha$) in the range of 20–60° and favorably, an angle ($\alpha$) in the range of 30–45° is formed between the axis of the tube body 2 and the axis of the side aperture connecting with each other the center of a virtual surface thereof flush with the inner peripheral surface side of the tube body 2 and the center of a virtual surface thereof flush with the peripheral surface of the tube body 2.

EXAMPLES

Examples of the present invention will be described in detail below.

Example 1

A catheter as shown in FIGS. 1 through 3 was manufactured to conduct clinical tests. The specification of the catheter is as follows:

Entire length: 10 cm

Outer diameter: 1.4 mm

Inner diameter (diameter of lumen): 1.0 mm

Length of soft tip part: 2 mm

Length of front flexible part: 18 mm

Configuration of side aperture: ellipse whose major axis is 0.5 mm, minor axis is 0.2 mm and which is perpendicular to the axial direction of catheter Number of side apertures: 12

Two side apertures are arranged in six rows in the lengthwise direction of the catheter. Every side aperture formed an equal angle 60° with the axis of the catheter.

Distance L between adjacent side apertures in axial direction of the catheter (distance between centers of side apertures of one row): 1.0 mm Inclination α of side apertures: equally 30°

Position of front end of side aperture-formed region: 2.3 mm rearward from the front end of the catheter Side aperture-forming method: formed by KrF excimer laser having an oscillation wavelength of 248 nm (power density on a surface of a workpiece: 0.5 kW/cm$^2$, irradiation time period for one side aperture: 2.3 seconds)

Material Constituting Tube Body

Inner layer and outer layer: Prepared by adding barium sulfate which is an X-ray opaque substance to a polymer alloy of polyamide elastomer and polyurethane.

Metal mesh: Metal mesh formed of stainless steel (diameter: 50 μm) was embedded in the boundary between inner layer and outer layers of the catheter in the entirety thereof except a region of 20 mm rearward from the front end of the catheter Soft tip part: Prepared by adding barium sulfate which is an X-ray opaque substance to polyurethane.

Material of base part: polyamide resin

Example 2

Another catheter of Example 2 as shown in FIGS. 8 through 10 has been manufactured, which is similar to that of Example 1 except that the conditions concerning the side apertures are changed as follows.

Configuration of side aperture: ellipse whose major axis is 0.5 mm, minor axis is 0.2 mm and which is long in the axial direction of catheter Number of side apertures:

Two side aperture are arranged in six rows in the lengthwise direction of the catheter. Every side aperture formed an equal angle 60° with the axis of the catheter.

Distance L between adjacent side apertures in axial direction of the catheter (distance between centers of side apertures of one row): 1.0 mm Inclination α of side apertures: equally 30°

Position of front end of side aperture-formed region: 2.3 mm rearward from the front end of the catheter Side aperture-forming method: formed by KrF excimer laser Experiment An experiment has been conducted on the catheters of Examples 1 and 2. The results about the catheters of Examples 1 and 2 are given as follows.

A guide wire was inserted into the lumen of the catheter. A sheath of 4F (1F=about ⅓ mm) was placed percutaneously in femoral arteries of 10 men of 55–65 years old. The catheter was inserted into the sheath. Then, the front end of the catheter was guided to the ascending artery, with the guide wire projecting forward from the front end of the catheter to insert the front end of the catheter into the inlet of the left coronary artery. Then, the guide wire was pulled out from the catheter. Then, a syringe was connected with the rear end of the rear part of the catheter to inject 5 ml of a contrast medium (Iomeron 350 (trade name), product of Ezai Corp., amount of iodine: 350 mg/ml) into the inlet of the left coronary artery at a pressure of 100 psi and a flow rate of 5 ml/sec. X-rays were applied to the bodies of the 10 men. It was observed that the contrast medium injected into the inlet of the left coronary artery was jetted toward the left coronary artery from the front end opening of the catheter and the side aperture.

A distinct image was obtained radiographically and favorable angiography of the left coronary artery could be accomplished. It was observed that a slight amount of the contrast medium leaked from the left coronary artery and that the front end of the catheter was not dislocated from the inlet of the left coronary artery.

According to the catheter of the present invention, a medical liquid (for example, contrast medium, liquid medicine, and the like) is injected into a desired part at a reduced speed; a liquid which has been introduced into the desired part can be prevented from flowing backward; a liquid discharged from the side aperture is jetted to the front end of the catheter. Therefore, the liquid discharged from the side aperture can be flowed into a desired blood vessel branch portion. Thus, supposing that the liquid is a contrast medium, it is possible to obtain stable angiographic performance without injecting much liquid, namely, the contrast medium into the desired part at a high pressure. Further, according to the catheter of the present invention, the liquid is discharged from the front end opening and the side aperture of the catheter. Thus, the liquid flows as a thick stream toward the desired part along the inner wall of a blood vessel, with the liquid being scattered favorably. Thus, even though the diameter of the catheter is small, it is possible to flow the liquid to the desired part uniformly. When the liquid is a contrast medium, the catheter provides high angiographic performance. When the liquid is a medicine, the catheter provides a favorable dispersibility of the medicine at the desired part.

What is claimed is:

1. A catheter for use in coronary angiography for performing a selective image formation by inserting a front end thereof into a coronary artery, the catheter having a front end for insertion into a coronary artery to deliver a X-ray contrast medium, said catheter comprising a tube body possessing a center line, the tube body being provided with a lumen, a front end opening communicating with the lumen, and a side aperture formed on a front end part of the tube body and communicating with the lumen, the side aperture possessing an axis and extending through a wall of the tube body so that the axis of the side aperture forms an oblique angle with respect to the center line of the tube body so that the side aperture is directed in a forward direction towards a front side of the tube body so that the X-ray contrast medium discharged from the side aperture is jetted forward of the side aperture and flows into the coronary artery, the tube body having an outer diameter that is 2.7 mm or less throughout the catheter, and the entire length of the tube body is 50 cm–125 cm.

2. A catheter according to claim 1, wherein a plurality of side apertures is formed at the front end part of the tube body.

3. A catheter according to claim 1, wherein the side aperture possesses an elliptical shape.

4. A catheter according to claim 1, wherein the side aperture forms an angle of 20°–60° with respect to the center line of the tube body.

5. A catheter specifically adapted for insertion of its front end into a coronary artery, said catheter comprising a tube body provided with a lumen extending from a rear end of the tube body towards a front end of the tube body through which medical liquid is adapted to flow, a front end opening communicating with the lumen, and a side aperture located at a front end part of the tube body and communicating with the lumen, the front end being constructed for insertion into the coronary artery, the side aperture being formed in the tube body and extending obliquely in a forward direction from an inner peripheral surface of the tube body to an outer peripheral surface of the tube body so that at least some medical liquid flowing through the lumen from the rear end of the tube body to the front end of the tube body flows through the side aperture and is directed forward of the side aperture toward a front side of the tube body so that the medical liquid discharged from the side aperture flows into the coronary artery, the tube body having an outer diameter that is 2.7 mm or less throughout the catheter, and the entire length of the tube body is 50 cm–125 cm.

6. A catheter according to claim 5, wherein a plurality of side apertures is located at the front end part of the tube body.

7. A catheter according to claim 5, further comprising a base part connected with the rear end of the tube body to allow medical liquid to be introduced into the lumen.

8. A catheter according to claim 5, wherein the side aperture forms an angle of 20°–60° with respect to an axis of the tube body.

9. A catheter according to claim 5, wherein the side aperture possesses an elliptical shape.

10. A catheter according to claim 5, wherein the catheter is an angiographic catheter.

11. A catheter according to claim 5, wherein the side aperture possesses an elliptical shape which is perpendicular to the axial direction of the catheter.

12. A catheter according to claim 5, wherein the side aperture possesses an elliptical shape which is elongated in an axial direction of the catheter.

13. A catheter specifically adapted for insertion of its front end into a coronary artery, said catheter comprising a tube body provided with a lumen extending from a rear end of the tube body towards a front end of the tube body through which medical liquid is adapted to flow, a front end opening communicating with the lumen, and a side aperture located at a front end part of the tube body and communicating with the lumen, the front end of the tube body having an outer diameter permitting the front end of the tube body to be inserted into a coronary artery, the side aperture being formed in the tube body and extending obliquely in a forward direction from an inner peripheral surface of the tube body to an outer peripheral surface of the tube body so that at least some medical liquid flowing through the lumen from the rear end of the tube body to the front end of the tube body flows through the side aperture and is directed forward of the side aperture toward a front side of the tube body so that the medical liquid discharged from the side aperture flows into the coronary artery, the tube body having an outer diameter that is 2.7 mm or less throughout the catheter, and the entire length of the tube body is 50 cm–125 cm.

14. The catheter according to claim 13, wherein the front end part of the tube body is provided with a plurality of side apertures communicating with the lumen, each of the side apertures forming an angle of 20°–60° with respect to the axis of the tube body.

15. The catheter according to claim 14, wherein the side apertures are elliptical.

16. The catheter according to claim 13, wherein the side aperture is formed in the shape of an ellipse which is perpendicular to the axial direction of the catheter.

17. A catheter according to claim 13, wherein the side aperture is formed in the shape of an ellipse that is elongated in an axial direction of said catheter.

18. The catheter according to claim 13, wherein the outer diameter of the front end of the tube body is 2.0 mm or less.

19. A catheter having a front end adapted to be inserted into a branch portion of a blood vessel and a tube body comprising a lumen, a front end, a front end opening communicating with said lumen, and side apertures formed in a side aperture forming region on a front end part of the tube body and communicating with said lumen, wherein said side apertures are obliquely formed from an inner peripheral surface of said tube body toward an outer peripheral surface thereof such that said side apertures are directed in a forward direction toward a front side of said tube body to allow a medical liquid discharged from each respective side aperture to be jetted forward of the respective aperture toward the front end of the tube body and flow into a desired blood vessel portion of said branch portion, a front end of said side aperture forming region is spaced at 1.5 mm to 2.5 mm from the front end of said tube body, the tube body having an outer diameter that is 2.7 mm or less throughout the catheter, and the entire length of the tube body is 50 cm–125 cm.

20. A catheter according to claim 1, further comprising a base part connected with a rear end of said tube body and allowing a liquid to be introduced into said lumen.

21. A catheter according to claim 1, wherein each of said side apertures forms an angle of 20°–60° with respect to an axis of said tube body.

22. A catheter according to claim 1, wherein said side apertures are elliptical.

23. A catheter according to claim 1, wherein said catheter is an angiographic catheter.

24. A catheter according to claim 22, wherein each of said side apertures is formed in the shape of an ellipse which is perpendicular to the axial direction of the catheter.

25. A catheter according to claim 22, wherein each of said side apertures is formed in the shape of an ellipse that is elongated in an axial direction of said catheter.

* * * * *

UNITED STATES PATENT AND TRADEMARK OFFICE
CERTIFICATE OF CORRECTION

PATENT NO. : 6,702,788 B2  Page 1 of 1
APPLICATION NO. : 09/282213
DATED : March 9, 2004
INVENTOR(S) : Taisei Kawakita et al.

It is certified that error appears in the above-identified patent and that said Letters Patent is hereby corrected as shown below:

Column 14, claim 20, line 47, change "1" to --19--.

Column 14, claim 21, line 50, change "1" to --19--.

Column 14, claim 22, line 53, change "1" to --19--.

Column 14, claim 23, line 55, change "1" to --19--.

Signed and Sealed this

Fifth Day of June, 2007

JON W. DUDAS
*Director of the United States Patent and Trademark Office*